United States Patent [19]

Tepic

[11] Patent Number: 4,463,875

[45] Date of Patent: Aug. 7, 1984

[54] METHOD AND APPARATUS FOR PREPARING AND APPLYING A TWO-COMPONENT CEMENT

[75] Inventor: Slobodan Tepic, Zagreb, Yugoslavia

[73] Assignees: Robert W. Mann, Cambridge, Mass.; Thomas Macirowski, Brooklyn, N.Y.; a part interest to each

[21] Appl. No.: 388,401

[22] Filed: Jun. 14, 1982

[51] Int. Cl.³ .......................... B67B 7/24; B67D 5/52
[52] U.S. Cl. ........................ 222/82; 222/94; 222/135; 222/196; 604/56; 604/87; 206/219
[58] Field of Search .................. 222/80-83, 222/94, 95, 105, 135, 137, 145, 196, 226, 243, 246, 386, 386.5, 541; 604/56, 82, 87, 89, 90, 92, 218, 240; 366/189, 190, 269; 141/74, 258-262; 206/219, 222; 215/DIG. 8

[56] References Cited

U.S. PATENT DOCUMENTS

| 1,928,998 | 10/1933 | Kovacs | 604/87 |
|---|---|---|---|
| 2,648,906 | 8/1953 | Holmes | 222/326 X |
| 2,998,036 | 8/1961 | Strasheim et al. | 141/74 X |
| 3,190,619 | 6/1965 | Penney et al. | 604/82 X |
| 3,195,778 | 7/1965 | Coates | 604/87 X |
| 3,351,058 | 11/1967 | Webb | 604/87 |
| 3,494,359 | 2/1970 | Zackheim | 222/137 X |
| 3,537,605 | 11/1970 | Solowey | 604/87 X |
| 3,700,215 | 10/1972 | Hardman et al. | 366/268 |

Primary Examiner—Joseph J. Rolla
Assistant Examiner—Michael S. Huppert
Attorney, Agent, or Firm—Cesari and McKenna

[57] ABSTRACT

To prepare and apply two-component cement, the components are vacuum-packaged in elongated flexible fluid-tight compartments and those compartments are confined in abutting relation with a seal existing around the abutting portions of the compartments. One of the compartments is gradually collapsed to force its contents to break through the abutting wall portions into the other compartment while the extension of the other compartment is controlled as it receives the one compartment contents so as to enhance the intimacy of contact between the cement components. Then the other compartment is gradually collapsed to force its contents into the one compartment while controlling the extension of the one compartment as it receives the other compartment contents so as to further mix the components. The two compartments are alternately collapsed and controlledly extended until the components therein form a homogeneous cementitious mixture. Then a nozzle is attached to one of the compartments in lieu of the other compartment and the one compartment is collapsed to expel the mixture through the nozzle to the deposition site. Specific apparatus for preparing and applying the cement is also disclosed.

21 Claims, 16 Drawing Figures

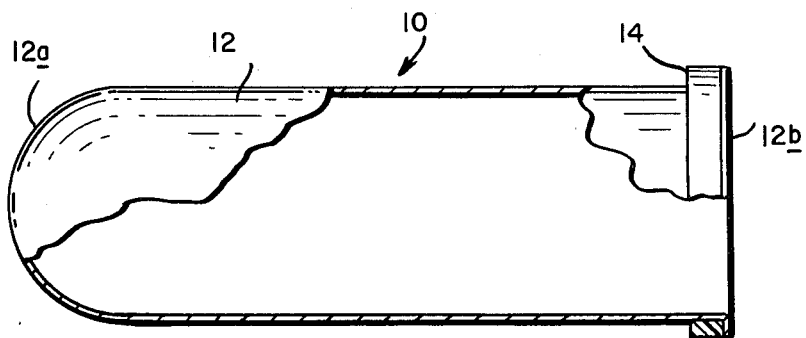
FIG. I
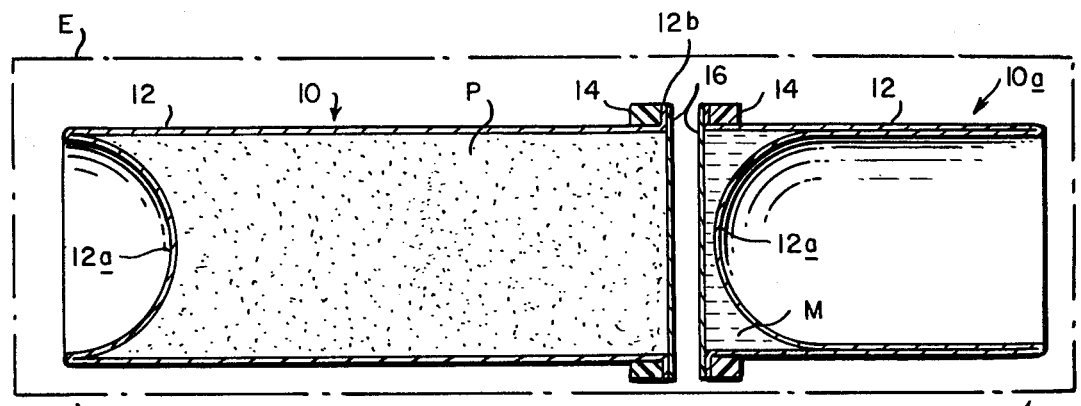
FIG. IA
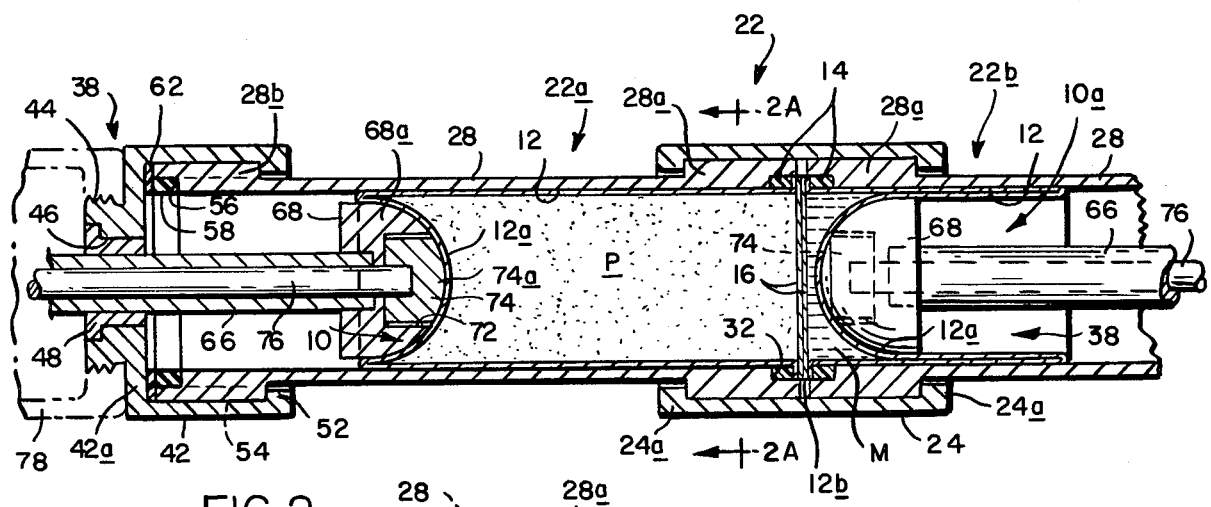
FIG. 2
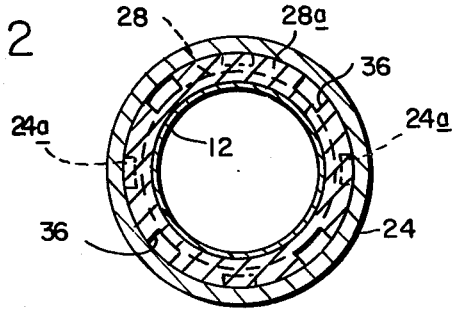
FIG. 2A

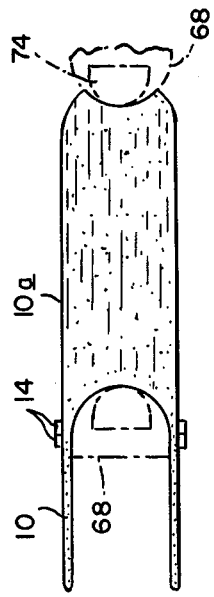
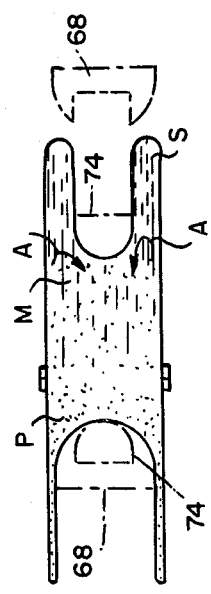
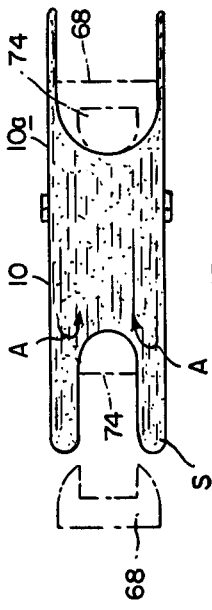
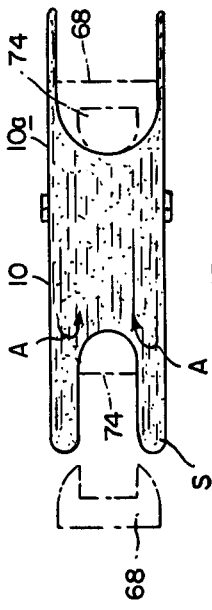
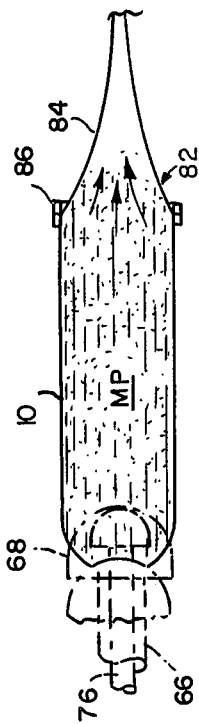
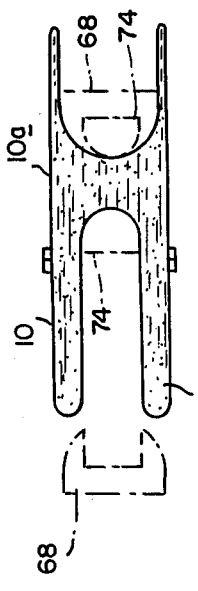
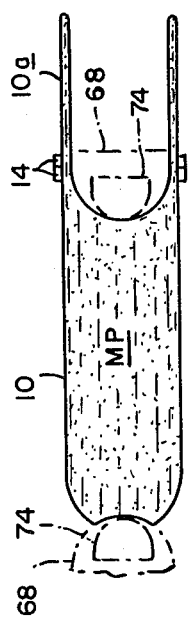

METHOD AND APPARATUS FOR PREPARING AND APPLYING A TWO-COMPONENT CEMENT

This invention relates to a method and apparatus for preparing and applying a cement composed of two components which polymerize when mixed together. The invention is especially useful in connection with a cement which is used to anchor and support artificial joint components in natural bone.

BACKGROUND OF THE INVENTION

Many modern day cements are composed of separate components which, when thoroughly mixed together, undergo a chemical reaction resulting in a substance which produces a very strong and effective bond between dissimilar objects. Various epoxy and acrylic cements fall into this category. In some cases, both components of the cement are liquids; in other cases, only one of the components is a liquid, the other being a powdered solid material.

While the present invention can be used to prepare and apply a variety of such cements, it is especially useful in the preparation and application of so-called bone cement used to anchor and support artificial joint components and other prostheses in natural bone. Accordingly, it will be described here specifically in that context.

The currently preferred bone cement is polymethylmethacrylate or so-called PMMA. PMMA is comprised of a powdered polymer and a liquid monomer catalyst. Upon mixing, these components polymerize within minutes so as to form a firm rigid bond between the prosthesis and the surrounding bone structure in which the prosthesis is placed.

The present procedure for preparing and applying PMMA bone cement is to remove the powdered catalyst and liquid catalyst from their separate containers and pour them into a mixing bowl, one after the other. Then the two cement components are mixed together by stirring them with an inert spatula. Usually, the mixing bowl is fitted with a vacuum device and a filterf to minimize the discharge of monomer vapors from the bowl. These vapors are toxic and could cause discomfort and injury to operating room personnel. The stirring process continues until the two components partially polymerize forming a substance having the consistency of putty or dough. That partially cured cement is then pressed into the bone structure in which the prosthesis is to be placed so as to form a bed for receiving the prosthesis.

For example, in a total hip replacement, a bed of cement is pressed into the patient's acetabulum by hand so as to form a bed for the acetabular component of the hip prosthesis. That component is a cup-like object which is usually made of plastic and defines a socket for receiving the femural component of the hip prosthesis. The latter is basically a ball formed at the end of a long stem. That stem is inserted into the patient's femural medullary canal after removal of the femural neck by known procedures. Prior to such insertion, the medullary canal is reamed out and packed with bone cement. Usually, the cement taken from the bowl is extruded into that canal under pressure using a cement gun or syringe which may be likened to a caulking gun. Then the stem of the femural prosthesis is inserted into the femural canal and positioned so that its ball is properly received in the acetabular component so as to allow a substantially full range of flexure of the new hip joint.

Not infrequently, one or both of the hip prostheses loosens, requiring reoperation to correct the failure. Sometimes, such loosening of the hip prosthesis has drastic consequences such as protrusion of the acetabulum or proximal femur fracture. In many cases, such failures have been traced to problems with the bone cement bond between the prosthesis and the bone structure.

More particularly, porosities or voids induced in the cement by the now-practiced mixing techniques cause a drastic reduction in its fatigue strength. Consequent cracking and fragmentation of the cement results in component loosening, almost invariably followed by various medical complications requiring a second surgical procedure. This porosity problem is widely recognized since, when mixing together the cement components in the mixing bowl, surgeons are cautioned not to whip or beat the mixture as that tends to produce pockets and voids which weaken the cement. However, even with careful mixing following normal procedures, a substantial number of pores and voids still remain in the cement body.

Also, if the cement body is to have a uniform strength throughout its extent, it is essential that the cement components be brought togethr as a homogeneous mixture so that the components throughout the mixture are in proper proportion. This is very difficult to do in a mixing bowl. Invariably, the degree of quality of the mixing varies according to the stirring motion used by the individual doing the mixing. A particular individual may stir for the requisite time to produce a partially polymerized cement mixture which overall has the proper consistency for placement in the body. However, small regions within that body may not polymerize completely because of inadequate mixing of the cement components in those regions. Those regions not only constitute weaknesses in the resultant cement bond, they also cause leakage of the unbound catalyst monomer, which is a toxic substance, into the surrounding bone structure. In fact, such leakage has already been identified as a major source of PMMA toxicity in such patients.

Still further, some problems with the bone cement bond can be attributed to the mode of applying the cement mixture to the bone structure prior to seating the prosthesis. As noted previously, the generally accepted technique for bedding the cement mixture is to press the dough-like substance into the bone structure or to extrude or inject it under static pressure using a cement syringe or gun. Even with the cement mixture well contrained in a bone cavity, which in practice is very hard to achieve, the influence of such statically applied pressure on cement penetration into bone is very limited. That influence cannot be increased by simply increasing the applied pressure without damaging the surrounding bone structure.

Finally, some of the prior apparatus used for this purpose are rather large and bulky and comprise several components, some of which are too expensive to be deemed disposable. Yet the removal of the polymerized cement from those parts after each use is time consuming and therefore also expensive.

SUMMARY OF THE INVENTION

Accordingly, the present invention aims to provide an improved method of preparing and applying a two-component cement.

Another object of the invention is to provide improved apparatus for preparing and applying such a cement.

Still another object of the invention is to provide such apparatus which thoroughly mixes the cement components so that all regions of the mixture have the proper component proportions to react chemically in the proper way.

Another object of the invention is to provide such apparatus which can mix the cement apparatus without the inclusion of air.

Yet another object of the invention is to provide apparatus of this general type which minimizes escape of toxic substances from the cement into the atmosphere.

A further object of the invention is to provide apparatus for preparing and applying a two-component cement to an object so as to create a bond of maximum strength between the cementitious body and the object.

Another object of the invention is to provide apparatus of that general type which thoroughly mixes the components of the cement and applies the cement in a consistent and reliable fashion.

Still another object of the invention is to provide such apparatus which is relatively compact and inexpensive to manufacture.

Yet another object is to provide such apparatus which is efficient and reliable and relatively easy to use.

Other objects will, in part, be obvious and will, in part, appear hereinafter.

The invention accordingly comprises the several steps and the relation of one or more of steps with respect to each of the others, and the apparatus embodying the features of construction, combinations of elements and arrangement of parts which are adapted to effect such steps, all as exemplified in the following detailed description, and the scope of the invention will be indicated in the claims.

Briefly, my method and apparatus are aimed at providing consistently well prepared and applied two-component cements, particularly bone cement. The two components of the cement are vacuum packed in separate flexible air-tight packaging compartments and mixed in situ without exposure to air, thereby avoiding gaseous inclusion and subsequent formation of pores in the cement.

In this, the flexible packaging compartments are juxtaposed within a fluid-tight mixer assembly so that a seal between the two cement components can be broken, permitting mixing of those components while still excluding the admission of any air into the mix.

The mixer assembly includes a pair of reciprocatable headed piston rods which collapse the two compartments alternately so that the cement components are pushed back and forth between the two compartments. The motion of these components is not a simple reciprocating motion, however. Rather, the collapsing and expanding of the two compartments is controlled so that the material in one compartment is forced to undergo a stirring, swirling motion as it is introduced into the other compartment. Resultantly, it is subjected to shear forces and eddies and is thereby brought into intimate contact with the material in the other compartment.

Then the piston rods are operated in reverse so that the partially-mixed contents of the second compartment is forced into the first compartment, again undergoing a stirring, swirling action in the process, thereby further increasing the intimacy of the contact between the two cement components. This process is repeated with the contents of one flexible compartment being stirred and swirled into the other compartment so as to create eddies in the mixture which progressively thoroughly mix all regions of the mixture.

It is important to note that during such mixing, the cement contacts only the flexible packaging containing the original cement components. Furthermore, the fluid-tight integrity of the packaging is maintained during this mixing. Therefore, no atmospheric air or other gases are introduced into the mixture which could produce pores or voids in the resultant body of cement. By the same token, any toxic vapors produced by the components of the cement remain trapped in the packaging during the entire mixing process.

The manipulation of the cement mixture back and forth between the two compartments is continued until the cement partially cures to form a substance of the proper consistency for application to the patient. Since the mixing of the cement components in the mixture is governed by the size and shapes of the compartments and piston rods and the number of piston extension cycles in a given time period, one can establish a definite procedure which will assuredly thoroughly mix those components in a reliable and consistent manner. No matter who operates the mixer, then, the mixingaction will be in the same from batch to batch so long as that procedure is followed.

As soon as the thoroughly mixed cement mixture has polymerized to its dough-like consistency, one compartment is collapsed by its piston so as to push the entire cementitious mixture into the other compartment. Then, that one compartment and its piston are detached from the mixer assembly and replaced by a disposable nozzle which is in fluid communication with the remaining compartment containing the cement mixture. Then, the remaining rod is extended to collapse that other compartment so as to extrude the cement mixture through the nozzle to the bone structure that is to receive the prosthesis. For example, if the cement is to be used to bond the femoral component of an artificial hip joint, the nozzle is inserted into the reamed-out femoral medullary canal and the piston rod actuated to extrude the mixture into that cavity until it is filled.

In a preferred embodiment of the invention, provision is made for applying a vibrating force to the cementitious mixture as it is being extruded through the nozzle. This vibratory force may be applied by vibrating the piston rod or the mixer body as a whole. In any event, supplementing the static pressure on the extruding mixture with such vibratory forces causes the cement mixture to penetrate relatively deeply into the surrounding bone pores. This is found to produce a strong intimate bond between the resultant cementitious body and the bone, without unduly stressing the bone structure.

In the event that the cement is being applied to a bond surface which is unconfined, a disposable fixture may be mounted at the end of the nozzle to contain and corral the cement mixture being extruded so that it is deposited only at the desired location on the bone structure, e.g. the surface of the acetabulum.

The present apparatus can even be used to help properly set an acetabular cup or prosthesis after the cement has been deposited in the acetabulum. In this, the piston can be detached from the mixer assembly. The head of the piston rod which has not come into contact with the cement components during the entire mixing and applying process can then be inserted into the acetabular cup socket and vibrated so as to exert a vibratory force on the cup. Alternatively, a differently sized head can be attached to that rod. In any event, the vibratory force is transmitted through the cup and the underlying cementitious material to the bone structure so that very strong intimate bonds are formed at the cup-cement-bone interfaces.

The apparatus to be described in detail which is used to implement the cement preparing and applying method disclosed herein is very small and compact and simple to operate. Most of the components of the apparatus can be reused repeatedly without recleaning after resterilization. The only components of the apparatus which do come into contact with the cement mixture are the disposable packaging for the cement components, the dispensing nozzle and the containing skirt or fixture. These are very simple molded plastic parts which are very easy and inexpensive to make in quantity. Therefore, the overall cost of the apparatus with its modular components is kept to a minimum. Accordingly, it should find wide application wherever it is necessary to prepare and apply two-component cements, especially bone cement.

BRIEF DESCRIPTION OF THE DRAWINGS

For a fuller understanding of the nature and objects of the invention, reference should be had to the following detailed description, taken in connection with the accompanying drawings, in which:

FIG. 1 is an elevational view with parts broken away showing a flexible package for containing a cement component to be mixed by the method and apparatus disclosed herein;

FIG. 1A illustrates two of the FIG. 1 packages juxtaposed, each containing one component of a two-component cement;

FIG. 2 is a sectional view illustrating apparatus for preparing and applying the cement components contained in the FIG. 1A packages;

FIG. 2 is a sectional view along line 2—2 of FIG. 2;

FIGS. 4A to 4H are diagrammatic views illustrating the operation of the FIGS. 2 and 3 apparatus to carry out the successive steps in the preparing and applying process described herein;

DESCRIPTION OF THE PREFERRED EMBODIMENTS

Figure 3:
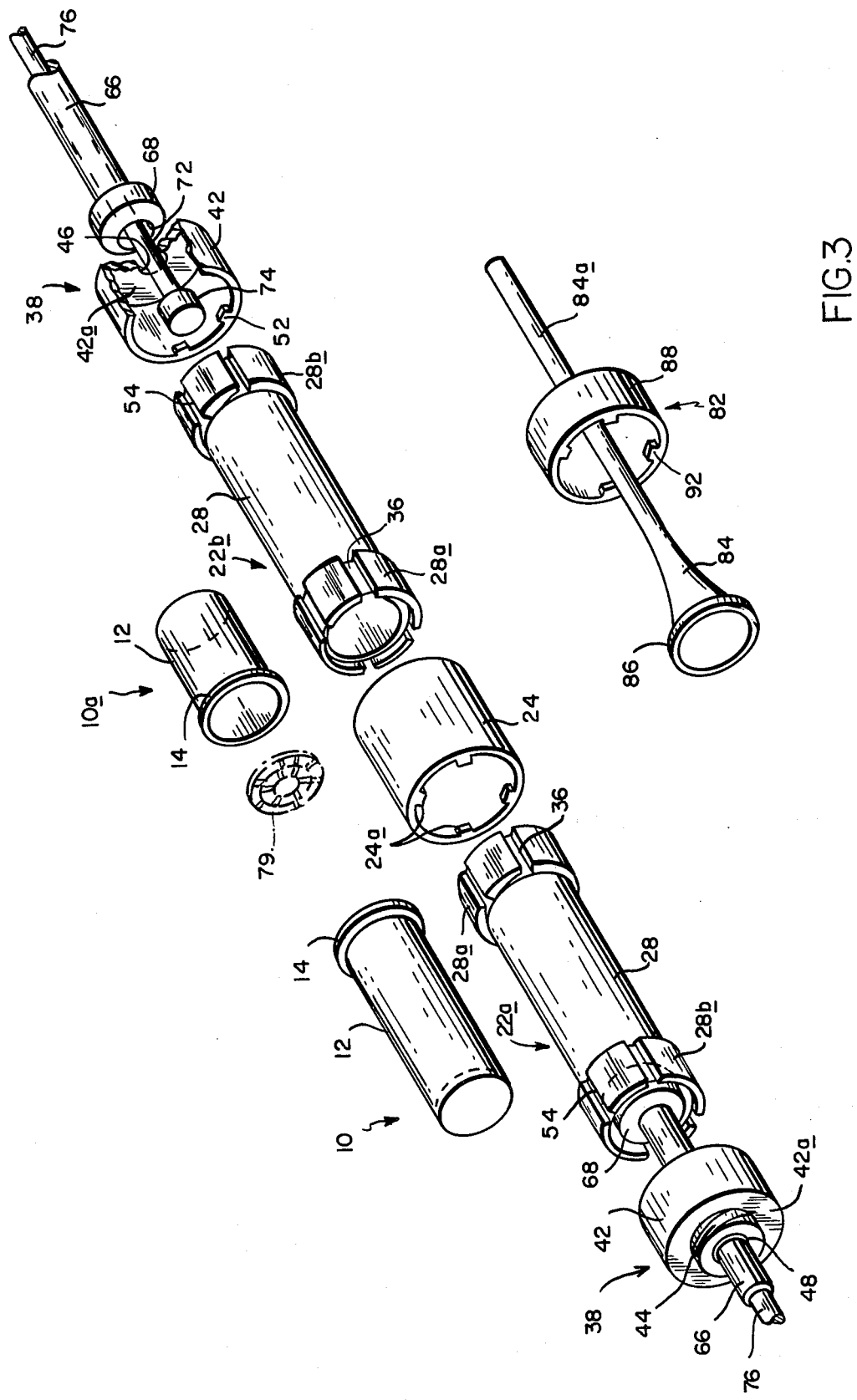
FIG. 3 is an exploded perspective view showing the components of the preparing and applying apparatus in greater detail.

Referring now to FIG. 1 of the drawings, each component of the two-component cement is packaged in a special, uniformly sized container or package shown generally at 10. Each container may comprise, for example, a tube 12 made of a flexible, resilient, air-tight, relatively tough material such as an appropriate grade of rubber. Alternatively, the tube may be a laminated structure with a tough resilient outer wall of rubber and an inner lining of impervious plastic.

The illustrated tube 12 has a closed rounded end 12a. The other tube end 12b is open, with the tube edges being engaged to the face of a resilient circular plastic ring or collar 14. Ring 14 performs positioning and sealing functions to be described later. As shown in FIG. 1A, the proper amount of one of the bone cement components, say, the powdered polymer P, is sterilized and vacuum packed in container 10 and the container is sealed by a penetrable or breakable fluid-tight discoid membrane or diaphragm 16 sealed around its edge margin to the tube end 12b. For example, the diaphragm may be made of sheet rubber, plastic, foil or the like. Preferably, the container 10 is not quite filled so that, when the vacuum is drawn, the tube end 12a is pulled inward on itself somewhat as shown in that figure.

Another similar package 10a containing the cement monomer component M is prepared in the same fashion. Component M is a liquid and only a small amount is required to produce, with component P, a proper cement mixture. Accordingly, the tube end 12a of container 10a is pulled in under vacuum to a much greater degree than that of container.

Alternatively, the two components M and P could be contained in separate compartments of a single package and kept isolated by a single diaphragm 16. In any event, the sterilized containers and their contents are then packaged in a sterile air-tight plastic envelope shown in dotted lines at E in FIG. 1A. Desirably, the envelope E should also be evacuated so as to make the air-tightness requirement of containers 10 and 10a less stringent and so as to increase the shelf life of the containers and their contents.

Referring now to FIGS. 2 and 2A, the two containers 10 and 10a are juxtaposed with their sealing diaphragms 16 in abutment in a mixing apparatus indicated generally at 22. Apparatus 22 comprises a pair of substantially indentical sections 22a and 22b which are coupled together by a sleeve 24. Preferably, these components are molded or otherwise formed of rugged impact-resistant plastic materials which are able to withstand autoclaving temperatures.

Each mixer section includes a cylindrical barrel 28 having opposite flanged ends 28a and 28b. The inner diameter of barrel 28 is sized to snugly receive a container 10 or 10a and its end flange 28a is counterboard at 32 to accommodate that container's ring 14. Thus, for example, in FIG. 2, prior to installation of the connector sleeve 24, the container 10 is snugly seated in mixer section 22a, while container 10a is similarly seated in section 22b. The two mixer sections may then be brought together with their diaphragms 16 in face-to-face contact as shown in FIG. 2 and coupled together by sleeve 24. When so coupled together, the two container rings 14 properly align the containers, while the edge margins of the abuting sealing diaphragms 16 and tube ends 12b provide a seal between the two containers so that no part of the containers contents can contact the sleeve 24 or barrels 28.

Sleeve 24 may coact to couple the barrels in a variety of different ways, a convenient one being the bayonnet-type of connection illustrated in FIGS. 2A and 3. For that, each barrel flange 28a is formed with a circular array of longitudinal grooves 36 and the opposite ends of sleeve 24 are formed with aligned circular arrays of radially inwardly-extending tabs or teeth 24a. The barrel flanges 28a can be brought together with their grooves 36 in alignment with each other and with the collar teeth 24a. When the two sections 22a and 22b abut as shown in FIG. 2, the sleeve 24 is rotated relative to the barrels so that the tabs 24a are offset from the grooves as shown in FIG. 2A, thereby locking the mixer sections together. The rings 14 and diaphragms 16 are sufficiently resilient that an effective annular seal is created between them when the collar 24 is in its locked position. Preferably also, the flange edge segments 28c facing teeth 24a are inclined in the locking direction as shown in FIG. 3 so that rotation of sleeve 24 tightly clamps the two mixer sections 22a and 22b together.

Referring now to FIGS. 2 and 3, each mixer section 22a and 22b also includes a piston assembly shown generally at 38. Assembly 38 comprises a cylindrical cap 42 having an end all 42a. Projecting axially from that wall is an exteriorly threaded neck 44 which is formed with a counterboard axial passage 46 for receiving a bushing 48. The opposite end of cap 42 has a circular array of radially inwardly-extending tabs or teeth 52 which form a bayonnet connection with a circular array of longitudinal grooves 54 in the associated barrel flange 28b. This bayonnet connection is exactly the same as the one depicted in FIG. 2A. In fact, the sleeve 24 and the cap 42 can be connected to either end of barrel 28. The end flange 28b is counterboard at 56 to receive a circular sealing rings 58 (FIG. 2 only). A gasket 62 (FIG. 2) may be provided at the inner surface of the cap end wall 42a so that, when the cap is coupled to the flange, an effective annular seal is present between the barrel and the cap.

Slidably received in the bushing 48 is a long tubular piston rod 66. Attached to the inner end of rod 66 is a head 68 having a rounded wall 68a facing away from the associated cap 42. A recess 72 is formed in that end wall for receiving a smaller head 74 which also has a rounded end wall 74a whose curvature corresponds to that of head wall 68a. Thus, when head 74 is seated in recess 72, a smooth generally semicircular surface is presented to the container 10 end wall 12a.

Head 74 is connected to one end of a piston rod 76 which extends through the tubular rod 66 as shown in FIG. 2. The coaxial rods 66 and 76 extend out from the end of the corresponding mixer section 22a or 22b where they may be connected to appropriate pistons (not shown) which can reciprocate the piston rods 66 and 76 independently of one another. Preferably, these pistons include structure for coupling to the threaded neck 44 of each cap 42 as indicated at dotted lines at 78 in FIG. 2. Alternatively, the outer ends of the piston rods 66 and 76 can terminate in handles so that they can be manipulated manually as will be described presently.

Turning now to FIGS. 4A to 4H, assume the container 10 and 10a are juxtaposed in the mixer as illustrated in FIGS. 2 and 4A with the powdered polymer P in the container 10 in the left-hand mixer section 22a and the liquid monomer M in the container 10a in the right-hand section 22b. To mix the components, the operator retracts the right-hand head 68 and maintains the smaller head 74 in its extended position as shown in FIG. 4B. Then he moves the head 68 (and head 74) in the left-hand mixer section 22a toward its extended position, i.e. to the right. This compresses container 10 and exerts sufficient pressure on the liquid therein to break the seals 16 between containers 10 and 10a. Accordingly, the polymer P is forced into container 10a and begins mixing with the liquid monomer M therein. The diameter of head 74 in section 22b is appreciably smaller than the inner diameter of container 10a so that a portion of the powdered polymer and the monomer are forced into an annular space S formed in container 10a outboard of head 74 as shown in FIG. 4B.

Referring now to FIG. 4C, as the operator continues to advance the left-hand head 68 toward the right, he retracts the right-hand head 74 so that the annular space S becomes progressively shorter. This produces a swirling action in the material in container 10a which applies shear forces to the mixture, creates eddies as shown by the arrows A in that figure and generally encourages are thorough mixing of the two cement components.

This swirling action imparted to the container contents as it is forced from one container to the other can be accentuated by inserting a baffle member with angled radial vanes between containers 10 and 10a inside sleeve 24. A baffle member such as this is illustrated in dotted lines at 79 in FIG. 3.

When the left-hand head 68 is in its fully extended position and the right-hand head 74 is in its fully retracted position as shown in FIG. 4D, the mixing motion is reversed. That is, the left-hand larger head 68 is retracted while its smaller counterpart 74 remains in the extended position. At the same time, the right-hand head 68 is advanced toward the left so that the monomer and polymer mixture is forced into an annular space S formed in container 10 as seen in FIG. 4E. Then the left-hand head 74 is gradually retracted as the right-hand head 68 is advanced so that space S becomes progressively shorter. This creates eddies and swirls in the mixture inside container 10 as shown by the arrows A in FIG. 4F, which intimately mix the cement components M and P even more.

The mixer repeats its alternate reciprocal compressions of the containers 10 and 10a, pushing the contents of one container into the other container in such a way as to swirl and stir the other container contents by virtue of the swirls and eddies formed therein due to the gradual retraction of the smaller piston head 74 in that other container, until eventually, as seen in FIG. 4G, all regions of the cement component mixture MP are mixed in the proper proportion. At that point, as shown in FIG. 4G, the right-hand head 68 can be extended and the left-hand heads 68 and 74 retracted so that the entire mixture MP is pushed into the left-hand container 10. Then, the sleeve 24 can be decoupled from the left-hand mixer section 22a are substituted for by a cement application section shown generally at 82 in FIGS. 3, 4 and 5. On the other hand, if the cement components are contained in a single two-component package, the right-hand compartment is cut away from the left-hand one at the sealing ring when installing section 82.

Figure 5:
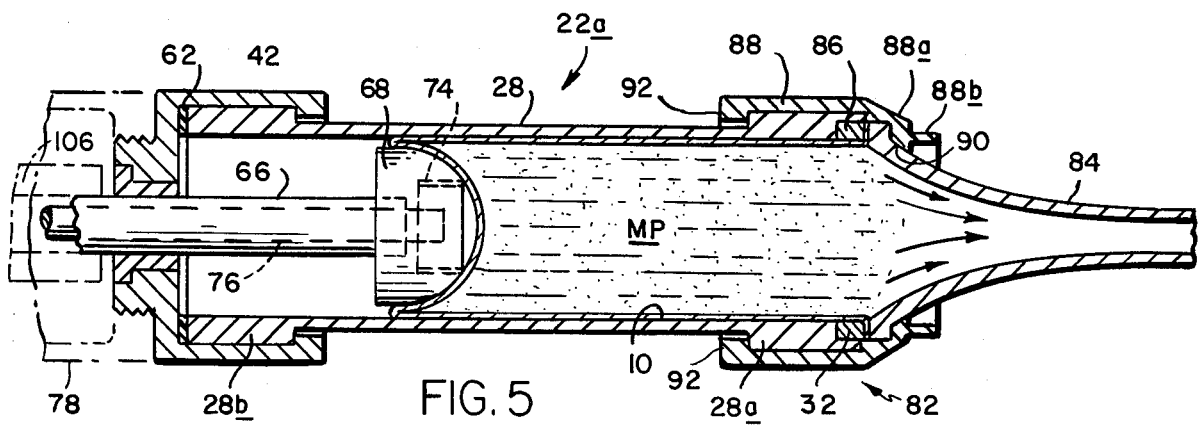
FIG. 5 is a sectional view showing the apparatus being used to apply the cementitious mixture.

As seen in FIGS. 3 and 5, section 82 comprises an inexpensive disposable plastic funnel or nozzle having a long stem 84a. The wider end of the nozzle is terminated by a positioning and sealing ring 86 similar to ring 14 on the container 10 or 10a. The nozzle is retained in place by a cap 88 having a central counterboard opening 90 (FIG. 5)in the cap wall 88a. The opposite cap end is formed with tabs or teeth 92 similar to teeth 24a on sleeve 24 and which slide through the flange grooves 36 in mixer section 22a, enabling the cap to be coupled to that section as best seen in FIG. 5. When ready, the cement mixture MP is expelled from container 10 through the nozzle 84 simply by advancing the left-hand head 68 toward the right in FIG. 5 so as to collapse container 10. The nozzle 84 is long enough so that its stem 84a can be inserted deep into hollow bone structure such as the femural medullary canal. The nozzle is gradually withdrawn from the canal as the extruded cement MP fills that cavity.

It is important to appreciate that, since the containers for the cement components are coupled together under vacuum during the entire mixing operation, no void-forming air is entrained in the mixture as might tend to weaken the cement bond. Furthermore, any volatile or toxic substances in those components do not escape from those containers. Therefore, no exhaust devices are required to protect nearby personnel from those fumes.

The replacement of sleeve 24 and section 22b with the nozzle assembly 82 after mixing is completed can be accomplished quite quickly so that minimal fumes escape to the atmosphere at that time. In this connection, it should be noted that the distal end of the nozzle stem 84a may be normally closed. The length of stem required for the application of the cement depends upon the cavity into which the cement is to be deposited. When the time comes to apply the cement, the nozzle stem is simply cut at the appropriate point along its length just prior to dispensing the cement.

It is also important to note that the heads 68 and 74 in conjunction with containers 10 and 10a impart the same type of mixing action to the cement components no matter who is operating the mixer. Therefore for any given cement formulation, a standard procedure in terms of the number of reciprocations within a given time interval can be adopted which produces optimal mixing of the components so that a cementitious mixture MP of the proper consistency is extruded through nozzle 84. This procedure may even be reduced to a table or chart which can be followed by any operating room personnel so that the quality and consistency of the cement applied to the bone site is uniform form one operation to the next.

Assuming that a total hip replacement operation is underway, once the cement mixture MP has been applied to the femural canal as described above in connection with FIG. 5, the stem of the femural prosthesis is inserted into that canal before the cement in the canal sets. When set, the cement contains no voids, pores or bubbles that constitute weak spots in the cementitious bond. Consequently, the prosthesis should not loosen even after prolonged usage.

Now the same procedure can be used to prepare and apply bone cement for the acetabular prosthesis or cup, preferably, after resterilizing the mixer 22 components. For this, the nozzle assembly 82 is removed by decoupling end cap 88 form the barrel flange 28a of section 22a. The nozzle 84 component of that assembly which has been contacted by the cement mixture can be disposed of; the cap 88, which has not been so exposed, can be retained and reused. The used container 10 is removed from mixer section 22, disposed of and replaced by a fresh container 10 filled with polymer P as shown in FIG. 1A. A fresh monomer 10a is then inserted into mixer section 22b and the two sections coupled together by sleeve 24 as described above. The same mixing process is then carried out so as to prepare a fresh batch of bone cement MP following the procedures discussed above in connection with FIGS. 4A to 4G. Then the sleeve 24 is decoupled from mixing section 28a and replaced by the application nozzle section 82 as described above in connection with FIGS. 4H and 5.

Figure 6:
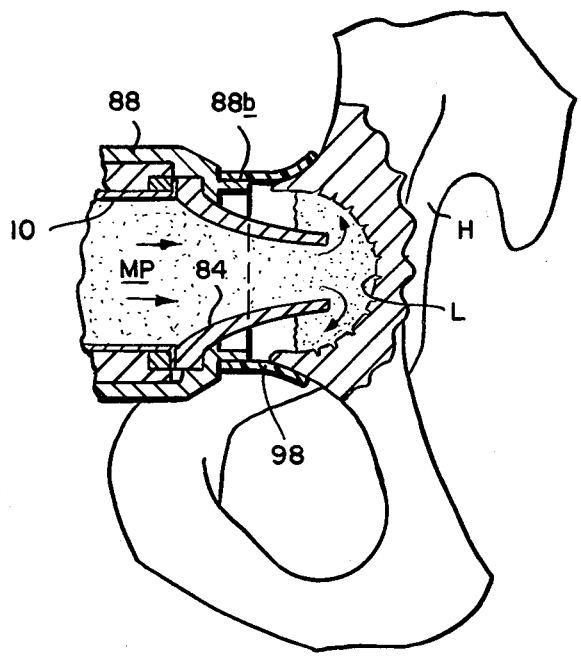
FIG. 6 is a similar view showing the apparatus depositing a cementitious mixture to the surface of the acetabulum during a total hip replacement operation.

Turning now to FIG. 6, the acetabularL is a concave socket or depression formed in the patient's hip bone H. Since that socket is relatively shallow, the nozzle 84 may be cut off quite near its wider end before the cement mixture MP is applied. Preferably, as shown in FIG. 6, cap 88 is formed with a reduced diameter and extension or skirt 88b on which is engaged a disposable flexible plastic sleeve 98 whose diameter varies according to the size of the cup being implanted. When the nozzle 84 is positioned in the acetabulum L, the edge of sleeve 98 engages the bone structure around that recess and may be connected thereto using bone staples, for example. Thus, when the cement mixture is deposited in the acetabulum, the sleeve 98 restricts the spreading of that mixture to the insertion site so that it is not applied to other bone surfaces.

Desirably, the sleeve 98 fits loosely on cap skirt 88b or one or more longitudinal grooves (not shown) are formed in the sleeve or skirt so that air can escape from the interior of the sleeve as the cement is delivered to the acetabulum L. As the cement fills the cavity, the nozzle may be withdrawn slowly from the sleeve 98. When the acetabulum L is filled, the nozzle 84 attached to mixer section 22a is removed, while the sleeve 98 remains attached to the bone.

Figure 7:
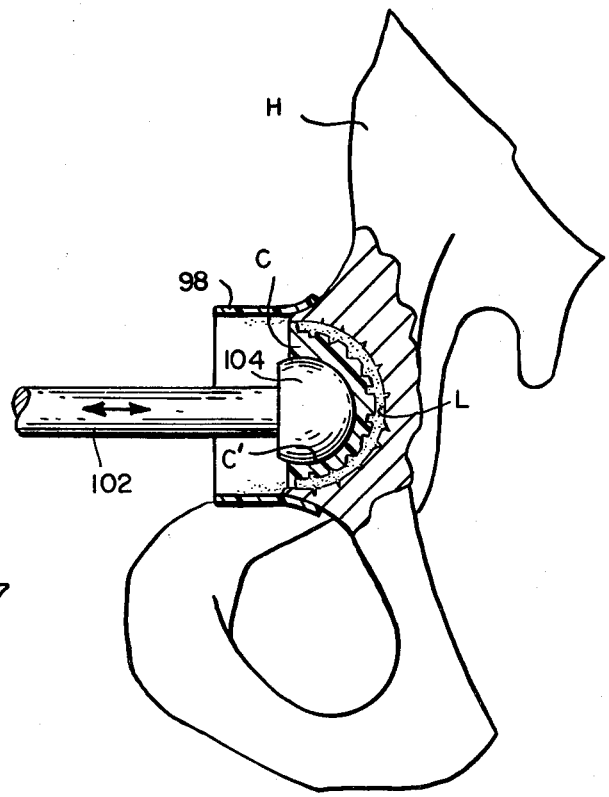
FIG. 7 is a similar view illustrating the apparatus used to set an acetabular cup into the mixture deposited as in FIG. 6.

Before the cement deposited in the acetabulum L has set, an acetabular prosthesis or cup C is positioned in that recess and pressed into place as depicted in FIG. 7. Acetabular cups are currently made of plastic material or ceramic material and sometimes have a metal case. In any event, the cup is a generally hemispherical object with a socket C' for receiving the ball of the femural hip prosthesis. If desired, the cup C can be pressed and held in place until the cement starts to cure by a rod 102 terminated by a ball 104 which fits the cup socket C'. Then the sleeve 98 can be removed, leaving the site of the cup insertion neat and clean. Actually, the rod 102 may be the piston rod 66 of section 22a, with the rod head 68 replaced by ball 104.

In some applications, it may be desirable to subject the cementitious material being applied to the patient's implantation site to a vibratory force in addition to the static pressure due to the advancing piston head 68. For this, a conventional vibrating mechanism 106 is connected via structure 78 to cap 42 as shown in FIG. 5 to impart a vibratory motion, say, at 60 Hz, to the piston rod 66 and its head 68. Accordingly, as the head advances to apply cement to tha site, it applies a vibratory force to the cement mixture MP in container 10 as it is being extruded and which supplements the static force. This vibratory force causes the cement mixture to penetrate relatively deeply into the pores present in the walls of the bone cavity into which the cement is being deposited. This procedure is found to produce an especially strong bond at the interface between the cement mass and the bone. Moreover, this small vibratory or dynamic pressure exerted on the cementitious mass causes that material to penetrate into the bone pores without rupturing or otherwise overly stressing the bone tissue.

A similar vibrator may be used to vibrate the rod 102 in FIG. 7 when setting the acetabular cup C. That vibratory motion which is transmitted to the cup and to the cementitious mass MP ensures intimate contact at both interfaces of the cement body.

It will be seen from the foregoing, then, that the above-described method of preparing and applying a two-component cement offers significant advantages over present day practices. From the time they are on the shelf until the mixing process is completed, the cement components remain sealed in their containers. Resultantly, no air or other gas can be entrained in the cement mixture as might adversely affect the resulting cement bond. By the same token, these personnel practicing the method and utilizing the apparatus are not subjected to noxious or toxic fumes or vapors emanating from the cement components.

Also, using the present method and apparatus, a precise procedure can be established for properly mixing the components of any particular cement, such as bone cement, so that upon the completion of the mixing process, all regions of the mixture are in the proper proportion to polymerize completing and the cementitious mixture as a whole has exactly the right quality and consistency for use. At that time, one mixer section of the apparatus can be replaced by a nozzle section, with the other mixer section being used to expel the mixture through the nozzle, preferably while imparting a vibratory motion to the cement mass. Resultantly, when deposited in the bone cavity, the cement penetrates into the pores of the cavity walls creating a very strong intimate bond therewith.

The apparatus for practicing the method is relatively inexpensive to make and maintain. The only components thereof which are contacted by cement are the cement component packages themselves and the dispensing nozzle and containng sleeve. Those are very simple disposable parts which can be made quite inexpensively in quantity. The remaining components of the mixing apparatus, while also comprised of inexpensive molded plastic parts, are never contacted by the cement. Therefore, they can be reused repeatedly after resterilization. Even the number of those parts is kept to a minimum since the apparatus is composed of two mixer sections which are identical and whose parts are interchangeable. Accordingly, that apparatus should find wide application whenever it is necessary to prepare and apply a two component cement such as polymethylmethacrylate bone cement.

It will thus be seen that the objects set forth above, among those made apparent from the preceding description, are efficiently attained, and, since certain changes may be made in carrying out the above method and in the construction set forth above without departing from the scope of the invention, it is intended that all matter contained in the above description or shown in the accompanying drawings be interpreted as illustrative and not in a limiting sense.

It is also to be understood that the following claims are intended to cover all of the generic and specific features of the invention herein described.

What is claimed as new and desired to be secured by Letters Patent of the United States is:

1. The method of preparing and applying a two-component cement comprising the steps of
   A. vacuum-packing the components in elongated flexible fluid-tight compartments;
   B. confining the compartments in abutting relation so that their longitudinal axes are collinear;
   C. establishing a seal around the abutting portions of the compartments;
   D. gradually collapsing one compartment to force its contents to break through said abutting portions into the other compartment, while controlling the extension of the other compartment along the direction of its said axis as it receives said one compartment contents so as to enhance the intimacy of contact between said components;
   E. gradually collapsing said other compartment along its said axis to force its said contents into said one compartment, while controlling the extension of said one compartment along its axis as it receives the other compartment contents so as to further enhance the mixing of said components;
   F. continuing the alternate collapsing and controlled extension of said compartments until said components form a homogeneous cementitious mixtue; and
   G. removing said mixture from said compartments.

2. The method defined in claim 1 wherein the extension of each compartment is controlled by
   A. permitting the extension of an annular volume of that compartment around its said axis while restraining the extension of a central volume of that compartment along its said axis so that the contents of the other compartment being collapsed is forced into said annular volume; and
   B. gradually permitting the axial extension of said central volume so that it gradually becomes available to receive said components.

3. The method defined in claim 1 wherein the removal of said mixture is accomplished by
   A. collapsing one of the compartments so as to force the mixture into the other compartment;
   B. separating the compartments;
   C. replacing the one compartment with a nozzle; and
   D. collapsing said other compartment so as to expel said mixture through said nozzle.

4. Apparatus for preparing and applying a two-component cement, each component being vacuum-packed in an elongated flexible fluid-tight compartment, said apparatus comprising
   A. means for confining the compartments in abutting relation so that their longitudinal axes are collinear;
   B. means for establishing a seal around the abutting portions of said compartments;
   C. means for gradually collapsing one compartment to force its contents to brak through said abutting portions into the other compartment;
   D. means for controlling the extension of said other compartment as it receives said one compartment contents so as to enhance the intimacy of the contact between said components;
   E. said extension-controlling means comprising plunger means slidably mounted to said confining means and movable in the direction of said axes so as to engage and retard the extension of said other compartment.

5. The apparatus defined in claim 4 and further including a pair of elongated flexible fluid-tight compartments confined in abutting relation by the confining means.

6. The apparatus defined in claim 5
   A. wherein said compartments are separate packages; and B. said seal-establishing means comprises gasket means incorporated into each compartment surrounding the area where it abuts the other compartment.

7. The apparatus defined in claim 5 wherein
   A. the compartments comprise a single package; and
   B. said seal-estalishing means comprises gasket means incorporated into the wall of said package intermediate its ends.

8. The apparatus defined in claim 4 wherein said collapsing means comprises second plunger means slidably mounted to said confining means and movable in the direction of said axes so as to engage and collapse said one compartment.

9. The apparatus defined in claim 4 wherein said confining means comprises
   A. a first tubular member containing one compartment;
   B. a second tubular member for containing the other compartment; and
   C. means for removably coupling said tubular members end to end so that the compartment therein are in abutting relation.

10. The apparatus defined in claim 9 and further including
    A. nozzle means having a relatively wide entrance end and a smaller exit end; and
    B. means for removably coupling the entrance end of said nozzle means to one of said tubular members in lieu of the other of said tubular members so that said nozzle means is in fluid communication with the compartment cntained in said one of said tubular members and so that the contents of the compartment contained in said one of said tubular members may be expelled through said nozzle means by sliding said plunger means.

11. The apparatus defined in claim 10 and further including
    A. tubular cement-confining means; and
    B. means for removably attaching said cement-containing means to said nozzle means so that said cement-confining means surrounds the exit end of said nozzle means.

12. The apparatus defined in claim 10 and further including means for vibrating said plunger means so as to impart vibrating forces to the contents being expelled through said nozzle.

13. Apparatus for preparing and applying a two-component cement, each component being vacuum-packed in an elongated flexible fluid-tight compartment, said apparatus comprising
    A. a pair of mixing sections, each section including
       1. an elongated rigid container for containing one of the compartments and having an open end,
       2. plunger means including first and second heads, and
       3. means for slidably mounting the plunger means in the opposite end of the container so that said first and second heads are movable independently of one another along the longitudinal axis of said container toward and away from said container open end; and
    B. means for removably coupling the open ends of said sections so that said sections are in axial alignment.

14. The apparatus defined in claim 13 and further including
    A. a first elongated, flexible, vacuum-packed, component-containing package positioned in one container, said package having a penetrable area adjacent the open end of said one container; and
    B. a second elongated, flexible, fluid-tight, component-containing package positioned in the other container, said second package having a penetrable area adjacent the open end of said other container, each said package having sealing means extending around the penetrable area thereof, said sealing means on the two packages being in sealing abutment when said containers are coupled together so as to prevent passage of fluids between the interiors of said packages and the containers.

15. The apparatus defined in claim 13 wherein each plunger means comprises
    A. an elongated tubular member extending axially into the associated compartment;
    B. an elongated rod member extending axially into the associated compartment through said tubular member;
    C. said first head being mounted to the inner end of said tubular member; and
    D. said second head being smaller than said first head and being mounted to the inner end of said rod member.

16. The apparatus defined in claim 15 and further including means facilitating the reciprocating of said rod and tube members independently of each other.

17. The apparatus defined in claim 15 wherein
    A. said first head is formed with a recess on the side thereof opposite said tubular member; and
    B. said second smaller head is receivable in said recess when said rod member is retracted relative to the tubular member.

18. The apparatus defined in claim 13 and further including
    A. a nozzle, said nozzle having
       1. a relatively wide entrance end,
       2. a smaller exit end, and
       3. a gasket extending around the periphery of said entrance end; and
    B. means for connecting the entrance end of the nozzle to the open end of one of the containers in lieu of said coupling means.

19. The apparatus defined in claim 18 and further including
    A. a skirt member; and
    B. means for attaching the skirt member to said nozzle so that it surrounds the exit end of the nozzle.

20. The apparatus defined in claim 18 and further including means for vibrating said plunger means of said one of said containers to which said nozzle is connected.

21. The apparatus defined in claim 13 wherein
    A. each container is formed with similar opposite end flanges;
    B. said container coupling means comprises a sleeve whose opposite ends couple to the flanges at the open ends of said compartments; and
    C. each said plunger mounting means comprises a cap which
       1. slidably rceives the associated plunger means tubular member, and
       2. couples to the opposite end flange of the associated container.

* * * * *